United States Patent
Reijnders et al.

(10) Patent No.: US 8,366,960 B2
(45) Date of Patent: Feb. 5, 2013

(54) PEROXIDE COMPOSITION

(75) Inventors: Johannes Martinus Gerardus Maria Reijnders, Epe (NL); Frederik Willem Karel Koers, Epse (NL)

(73) Assignee: Akzo Nobel N.V., Arnhem (NL)

( * ) Notice: Subject to any disclaimer, the term of this patent is extended or adjusted under 35 U.S.C. 154(b) by 0 days.

(21) Appl. No.: 12/594,067

(22) PCT Filed: Apr. 10, 2008

(86) PCT No.: PCT/EP2008/054351
§ 371 (c)(1),
(2), (4) Date: Sep. 30, 2009

(87) PCT Pub. No.: WO2008/125591
PCT Pub. Date: Oct. 23, 2008

(65) Prior Publication Data
US 2010/0113726 A1   May 6, 2010

Related U.S. Application Data

(60) Provisional application No. 60/926,355, filed on Apr. 26, 2007.

(30) Foreign Application Priority Data

Apr. 13, 2007  (EP) ..................... 07106154

(51) Int. Cl.
*C08F 4/34* (2006.01)
(52) U.S. Cl. ......... 252/186.42; 252/186.26; 252/182.23; 525/387; 525/330.3; 526/227
(58) Field of Classification Search ............. 252/186.26, 252/186.42, 182.23; 525/387, 330.3; 526/227
See application file for complete search history.

(56) References Cited

U.S. PATENT DOCUMENTS

| 3,222,294 A | 12/1965 | Meyer |
| 3,349,040 A | 10/1967 | Kresssin |
| 5,690,856 A * | 11/1997 | Milleville et al. ........ 252/186.26 |

FOREIGN PATENT DOCUMENTS

| DE | 207 728 | 3/1984 |
| GB | 834373 | 5/1960 |
| GB | 1072728 | 6/1967 |
| GB | 1 334 289 | 10/1973 |
| GB | 1334289 | * 10/1973 |
| JP | 57-040507 | * 3/1982 |
| WO | WO 99/57191 | 11/1999 |
| WO | WO 02/14383 | 2/2002 |

OTHER PUBLICATIONS

Akzo Nobel Brochure, "Initiators for High Polymers."
Allan Barton, *CRC Handbook of Solubility Parameters and Other Cohesion Parameters*, Second Ed. 1991.
International Search Report and Written Opinion, International PCT Application No. PCT/EP2008/054351, mailed Jul. 10, 2008.
International Preliminary Report on Patentability, International PCT Application No. PCT/ EP2008/054351, mailed Oct. 13, 2009.
"Silica," *Kirk-Othmer Encyclopedia of Chemical Technology*, Chapter 4.1, vol. 22, [published online on Jun. 16, 2006].

* cited by examiner

*Primary Examiner* — Roberto Rabago
(74) *Attorney, Agent, or Firm* — Robert C. Morriss

(57) ABSTRACT

The invention pertains to a peroxide composition comprising, based on the total weight of the composition: a) 10-90 wt % of an organic peroxide; b) 90-10 wt % of an organic solvent in which the organic peroxide does not dissolve; and c) optionally additives; wherein the water content is less than 20 wt %.

18 Claims, No Drawings

PEROXIDE COMPOSITION

REFERENCE TO RELATED APPLICATION(s)

This application is the U.S. National Phase of PCT/EP2008/054351 filed on Apr. 10, 2008 and claims the benefit of U.S. Provisional Application No. 60/926,355 filed on Apr. 26, 2007.

The present invention relates to peroxide compositions comprising an organic peroxide.

Such peroxide compositions are known in the art. In particular, peroxide compositions containing water as suspending medium have been found to form storage stable peroxide formulations. The use of water as suspending medium is undesirable in some applications as water may influence the curing properties—the compositions may not cure at all—and water may impair the mechanical properties of the resulting polymer. Moreover, water is not compatible with apolar organic polymer systems, and will separate out.

It is therefore an object of the present invention to provide peroxide formulations which are storage stable, contain a reduced amount of water, and which do not have the disadvantages described above for conventional water-containing peroxide compositions.

This object is achieved by providing a peroxide composition comprising, based on the total weight of the composition:
a) 10-90 wt % of an organic peroxide;
b) 90-10 wt % of an organic solvent in which the organic peroxide does not dissolve; and
c) optionally additives;
wherein the water content is less than 20 wt %.

The use of the organic solvent in the peroxide composition of the invention provides peroxide compositions which are storage stable. These compositions contain considerably less water than conventional peroxide compositions, and the invention also allows stable peroxide compositions that are free of water. Moreover, the activity of the peroxide composition—in terms of active oxygen content (AO)—is hardly reduced over time if at all. Furthermore, the change in average particle size of the peroxide droplets, which are either liquid or solid, is similar to or smaller than for conventional aqueous peroxide compositions. Furthermore, the viscosity of the peroxide compositions of the invention hardly changes over a prolonged period of time if at all.

The invention allows organic peroxides that are solid at room temperature to be transferred easily in liquid suspensions which are readily pumpable and easy to dose to a polymerization mixture.

The organic peroxide which can suitably be used in the composition of the invention can be any organic peroxide known in the art. The organic peroxide does not dissolve in the organic solvent of the peroxide composition of the invention. In the context of the present application the phrase "does not dissolve" means that less than 5 g/l of the organic peroxide is dissolved in the organic solvent. Preferably, less than 2 g/l is dissolved, more preferably less than 1 g/l, and most preferably less than 0.1 g/l of the organic peroxide is dissolved in the organic solvent.

The organic peroxide can be a peroxyester, a peroxycarbonate, a peroxydicarbonate, a ketone peroxide, a diacyl peroxide, a dialkyl peroxide, a trioxepan as disclosed in European Patent Application No. 00203888.3, cyclic peroxides, and dimers, trimers, and polymers of the aforementioned peroxides. It is also contemplated to use a combination of two or more organic peroxides. Examples of organic peroxides can be found in the brochure "Initiators for High Polymers" with code 1000225 of Akzo Nobel Chemicals.

The peroxide can be liquid at room temperature or solid at room temperature. The invention is particularly suitable for organic peroxides that are solid at room temperature. Examples of organic peroxides that are solid at room temperature include di(4-tertbutylcyclohexyl) peroxydicarbonate, dicetyl peroxydicarbonate, dimyristyl peroxydicarbonate, dilauroyl peroxide, didecanoyl peroxide, dibenzoyl peroxide, 1,4-di(tert-butyl peroxycarbo)cyclohexane, dicumyl peroxide, and di(tert-butyl peroxyisopropyl)benzene. Cyclohexanone peroxide is also solid at room temperature, but is less preferred as it generally dissolves in organic solvents suitably used in the compositions of the invention, such as the solutions described in DD 207728.

The organic peroxide is generally present in the composition of the invention in an amount of at least 10 wt %, preferably at least 15 wt %, and most preferably at least 20 wt %, based on the total weight of he composition, and generally at most 90 wt %, preferably at most 70 wt %, and most preferably at most 50 wt %, based on the total weight of the composition.

The organic solvent is generally a solvent in which the liquid and/or solid organic peroxide can be dispersed and in which the organic peroxide does not dissolve. If the organic peroxide is liquid and combined with a liquid organic solvent, the peroxide composition is referred to as an emulsion. In another embodiment, the organic peroxide is solid and the organic solvent is liquid; in such case the peroxide composition is referred to as a suspension.

In one embodiment of the invention, the organic solvent has a $\delta(p)$ of at least 8, a $\delta(d)$ of at most 19, and a $\delta(h)$ of between 6 an 20. $\delta(p)$, $\delta(d)$, and $\delta(h)$ are also known as Hansen solubility parameters. More information can be found in Allan Barton, *CRC Handbook of Solubility Parameters and Other Cohesion Parameters*. In another embodiment of the invention, the organic solvent of the invention comprises at least one hydroxyl group and/or at least one —OR group, wherein R is a substituent comprising from 1 to 20 carbon atoms. The R-group may contain one or more heteroatoms like O, N, or S.

The organic solvent generally does not react with the peroxide or with itself in the presence of the organic peroxide. For this reason, organic solvents comprising a nitrogen atom are less preferred. Suitable examples of organic solvents include glycols such as ethylene glycol, glycerol, diethylene glycol, dipropylene glycol, polyethylene glycol, and polypropylene glycol; alkoxylated alcohols such as propylene glycol monomethyl ether, propylene glycol monoethyl ether, and butyl dioxytol (also known as diethylene glycol monobutyl ether, formula $nBuOCH_2CH_2OCH_2CH_2OH$); and phosphorus-containing compounds such as diethyl phosphate, dibutyl phosphate, tributyl phosphate, triethyl phosphate, dibutyl phosphite, and triethyl phosphite.

Preferred organic solvents are selected from the group consisting of ethylene glycol, glycerol, diethylene glycol, dipropylene glycol, polyethylene glycol, triethyl phosphate, and butyl dioxytol.

It is also contemplated to use a combination of two or more organic solvents. Organic solvents comprising an —OR group and a propylene group, in particular polypropylene glycol, are less preferred.

The organic solvent is generally present in the composition of the invention in an amount of at least 10 wt %, preferably at least 15 wt %, and most preferably at least 20 wt %, based on the total weight of the composition, and generally of at most 90 wt %, preferably at most 70 wt %, and most preferably at most 50 wt %, based on the total weight of the composition.

The peroxide composition of the present invention generally comprises less than 20 wt % of water, based on the total weight of the composition. Preferably, the composition comprises less than 10 wt % of water, more preferably less than 5 wt %, and most preferably the composition is free of water.

The peroxide composition of the invention optionally may comprise additives. These additives are generally known in the art and used in conventional peroxide compositions. Examples of such additives include anti-freezing agents, (non-ionic) surfactants, emulsifiers, protective colloids, thickeners, pH-adjusting agents such as calcium oxide or phosphate buffers, sequestering agents, and, if desired, biocides, e.g. fungicides. The concentration of these additives will depend on the desired effect and the other ingredients in the peroxide composition.

Less preferred additives are phthalates and benzoates like 2-ethylhexyl benzoate, as these generally form an undesirable environmental burden and/or are carcinogenic.

Generally, the additive is present in an amount of at least 0.1 wt %, preferably at least 0.5 wt %, and most preferably at least 1 wt %, based on the total weight of the peroxide composition, and generally of at most 20 wt %, preferably at most 10 wt %, and most preferably at most 5 wt %, based on the total weight of the peroxide composition.

As is well-known, peroxides are thermally labile organic compounds. Because the decomposition of peroxide is exothermic, it is hazardous when the heat of decomposition cannot be dissipated, e.g., by heat loss to the surrounding area. When heat build-up occurs, the decomposition reaction eventually becomes uncontrollable and potentially dangerous. It is therefore highly undesirable that peroxide compositions show phase separation, as this means that the peroxide separates out and forms a highly concentrated peroxide phase the heat of decomposition of which is not dissipated. As a result, such peroxide compositions can be as hazardous as the neat peroxide. One of the objects of the emulsions according to the invention therefore was to develop formulations that do not form a significant amount of a hazardous phase upon heating.

A composition in accordance with the invention is considered to be safe if less than 10% by volume of one or more other phases is formed or, if more than 10% by volume of phase separation should occur, none of the phases has a peroxide content such that the active oxygen content is greater than 1 wt %. In a discriminating test for "safe" behaviour a sample of the composition is kept at a temperature which is 35° C. above the well-known self-accelerating decomposition temperature (SADT) of the peroxide phase present in the composition for 8 hours.

The compositions of the invention can be used in polymer modification processes, cross-linking reactions, mass polymerization processes, and curing processes of, for example, unsaturated polyester resins. In these processes a variety of monomers and/or polymers can be reacted, including, for example, acrylates, vinyl esters, vinyl halides, vinyl ethers, vinyl aromatic compounds, such as styrene, lower alkenes, polybutadiene, methacrylate-butadiene-styrene copolymers, and the like.

The peroxide compositions of the invention are suitably used in mass polymerization processes, and in particular in the curing of unsaturated polyester resins or acrylate resins.

The present invention is illustrated with the following Examples.

EXAMPLES

The ingredients used in the peroxide compositions of the Examples are presented in the following Table.

| | |
|---|---|
| PEG | Polyethylene glycol (molecular weight is about 200) ex Baker |
| DEG | Diethylene glycol ex Baker |
| EG | Ethylene glycol ex Baker |
| DG | Diglycerol ex Solvay |
| TEP | Triethyl phosphate ex Lanxess |
| Perkadox 16 | di-(4-tert-butyl cyclohexyl) peroxydicarbonate ex Akzo Nobel |
| Perkadox L-W75 | Benzoyl peroxide ex Akzo Nobel |
| Aerosil 200 | Fumed silica ex Degussa |
| Tergitol XD | Polyalkylene glycol ether ex Union Carbide |

The active oxygen content of the peroxide compositions was determined using standard method of analysis Jo/92.1. This standard method of analysis is available from Akzo Nobel Polymer Chemicals. From the active oxygen content the assay of the peroxide in the formulation can be calculated, which is expressed in wt % based on the total weight of the formulation.

The viscosity of the compositions was determined using a Physica US200/32 V2.50 MC100 VT 100 (MP 31 (50 mm, 0°) d=1 mm; constant shear rate=5 $s^{-1}$; at 20° C.). The viscosity is expressed in mPa·s.

Examples 1-6

Various peroxide suspensions in accordance with the present invention were prepared. Their compositions are shown in Table 1 below.

TABLE 1

| Ingredient | 1 | 2 | 3 | 4 | 5 | 6 |
|---|---|---|---|---|---|---|
| | | | Amount (wt %) | | | |
| PEG | 47.1 | 47.1 | 11.1 | | 11.1 | |
| DEG | | 11.1 | 47.1 | 47.1 | | 11.1 |
| EG | 11.1 | | | 11.1 | 47.1 | 47.1 |
| Perkadox 16 | 40 | 40 | 40 | 40 | 40 | 40 |
| Aerosil 200 | 1.8 | 1.8 | 1.8 | 1.8 | 1.8 | 1.8 |
| | | | After 1 week at 30° C. | | | |
| Separation | no | no | no | No | no | no |
| Assay (wt %) | 40 | 41 | 40 | 39 | 38 | 41 |
| Viscosity (mPa·s) | 7,800–8,000 | 7,500–7,800 | 4,500–4,700 | 6,300–6,800 | 5,400–5,800 | 5,200–5,800 |

It can be deduced from the Table that the suspensions of Examples 1 through 6 have a good storage stability at 30° C. After one week at this temperature the peroxide compositions do not show any separation of peroxide. Moreover, the active oxygen content of the compositions generally remains constant.

Examples 7-9

Various peroxide suspensions in accordance with the present invention were prepared, their ingredients are shown in Table 2 below.

TABLE 2

| Ingredient | 7 | 8 | 9 |
|---|---|---|---|
| | | Amount (wt %) | |
| DG | 20 | 25 | 15 |
| TEP | 14.5 | 10 | 19 |
| Aerosil 200 | 1.5 | 1.0 | 2.0 |
| Perkadox L-W75 | 53.3 | 53.5 | 53.3 |
| DEG | 10.6 | 10.6 | 10.6 |
| Tergitol XD | 0.1 | 0.1 | 0.1 |
| After 1 week at 40° C. | | | |
| Separation | no | no | no |
| Assay (wt %) | 39.5 | 39.7 | 39.4 |
| Viscosity (mPa · s) | 1,400-1,600 | 1,200-1,400 | 1,300-1,500 |

It can be deduced from the Table that the suspensions of Examples 7-9 have a good storage stability at 40° C. After one week at this temperature the peroxide composition does not show any separation of peroxide. Moreover, the active oxygen content of the compositions decreases at an acceptable level.

The invention claimed is:

1. A peroxide composition comprising, based on the total weight of the composition:
    a) 10-90 wt % of an organic peroxide;
    b) 90-10 wt % of an organic solvent in which the organic peroxide does not dissolve, the organic solvent selected from trialkyl phosphates, alkoxylated alcohols, and glycols: and
    c) 1-2 wt % of an hydrophilic fumed silica;
wherein the water content is less than 20 wt %; and with the proviso that, if the peroxide composition contains a combination of different organic solvents, the organic peroxide does not dissolve in the organic solvent combination contained in the peroxide composition.

2. The peroxide composition according to claim 1 wherein the organic solvent has a δ(p) of at least 8, a δ(d) of at most 19, and a δ(h) of between 6 and 20.

3. The peroxide composition according to claim 1 wherein the organic solvent comprises at least one hydroxyl and/or at least one —OR group, wherein R is a substituent comprising from 1 to 20 carbon atoms.

4. A process comprising a step of mass polymerization using the peroxide composition according to claim 1.

5. A method comprising a step of curing unsaturated polyester resins or acrylate resins, using a peroxide composition according to claim 1.

6. The peroxide composition according to claim 1, wherein the organic peroxide is 1,4-di(tert-butyl peroxycarbo)cyclohexane.

7. The peroxide composition according to claim 6, wherein the organic solvent is one or more glycols.

8. The peroxide composition according to claim 7, wherein the organic solvent is at least two glycols selected from PEG, DEG and EG.

9. The peroxide composition according to claim 1, wherein the composition consists essentially of, based on the total weight of the composition:
    a) 10-90 wt % of the organic peroxide;
    b) 90-10 wt % of the organic solvent:
    c) 1-2 wt % of the hydrophilic fumed silica; and
    d) zero to less than 20 wt % water.

10. The peroxide composition according to claim 9, wherein the organic solvent is one or more glycols.

11. The peroxide composition according to claim 10, wherein the organic solvent is a combination of at least two glycols selected from PEG, DEG and EG.

12. A peroxide composition comprising, based on the total weight of the composition:
    a) 10-90 wt % of an organic peroxide;
    b) 90-10 wt % of an organic solvent in which the organic peroxide does not dissolve, the organic solvent being a combination of at least two organic solvents, wherein the combination contains at least one trialkyl phosphate and at least one glycol: and
    c) 1-2 wt % of an hydrophilic fumed silica;
wherein the water content is less than 20 wt %.

13. The peroxide composition according to claim 12, wherein the organic solvent combination further comprises at least one alkoxylated alcohol.

14. The peroxide composition according to claim 13, wherein the organic peroxide is dibenzoyl peroxide.

15. The peroxide composition according to claim 14, wherein the at least one trialkyl phosphate is triethyl phosphate; the at least one glycol is chosen from ethylene glycol, glycerol, diethylene glycol, dipropylene glycol, polyethylene glycol and combinations thereof; and the at least one alkoxylated alcohol is butyl dioxytol.

16. The peroxide composition according to claim 13, wherein the composition consists essentially of, based on the total weight of the composition:
    a) 10-90 wt % of the organic peroxide;
    b) 90-10 wt % of the organic solvent:
    c) 1-2 wt % of the hydrophilic fumed silica; and
    d) zero to less than 20 wt % water.

17. The peroxide composition according to claim 16, wherein the organic peroxide is dibenzoyl peroxide.

18. The peroxide composition according to claim 17, wherein the organic solvent is a combination of triethyl phosphate, glycerol, diethylene glycol, and butyl dioxytol.

* * * * *